(12) United States Patent
Aleman et al.

(10) Patent No.: US 6,191,137 B1
(45) Date of Patent: Feb. 20, 2001

(54) PHARMACEUTICAL COMPOSITION FOR ORAL ADMINISTRATION

(75) Inventors: Claude Aleman; Philippe Bastard, both of Montpellier; Marielle Bonnel, Couronsec; Thierry Breul, Montpellier, all of (FR)

(73) Assignee: Sanofi-Synthelabo, Paris (FR)

(*) Notice: Under 35 U.S.C. 154(b), the term of this patent shall be extended for 0 days.

(21) Appl. No.: 09/581,718

(22) PCT Filed: Dec. 14, 1998

(86) PCT No.: PCT/FR98/02712

§ 371 Date: Jun. 16, 2000

§ 102(e) Date: Jun. 16, 2000

(87) PCT Pub. No.: WO99/33466

PCT Pub. Date: Jul. 8, 1999

(30) Foreign Application Priority Data

Dec. 24, 1997 (FR) .................................................. 97 16529

(51) Int. Cl.$^7$ ...................................................... A61K 31/435
(52) U.S. Cl. ................................................................ 514/277
(58) Field of Search ............................................... 514/277

(56) References Cited

U.S. PATENT DOCUMENTS 5,378,709    1/1995    Manning et al. .

*Primary Examiner*—Raymond Henley, III
(74) *Attorney, Agent, or Firm*—Michael D. Alexander; Paul E. Dupont

(57) ABSTRACT

The present invention relates to an aqueous solution containing 1-[2-(2-naphthyl)ethyl]-4-(3-trifluoromethylphenyl)-1,2,3,6-tetrahydropyridine hydrochloride (hydrochloride of SR 57746), also comprising β-cyclodextrin (β-CD) and a pharmaceutically acceptable acid or buffer to give a pH of less than or equal to 3.

21 Claims, No Drawings

PHARMACEUTICAL COMPOSITION FOR ORAL ADMINISTRATION

This is a 371 of PCT/FR98/02712 filed Dec. 14, 1998.

The present invention relates to a drinkable oral pharmaceutical composition containing 1-[2-(2-naphthyl)ethyl]-4-(3-trifluoromethylphenyl)-1,2,3,6-tetrahydropyridine hydrochloride.

More specifically, the invention relates to a drinkable composition of 1-[2-(2-naphthyl)ethyl]-4-(3-trifluoromethylphenyl)-1,2,3,6-tetrahydropyridine hydrochloride in aqueous solution with β-cyclodextrin at an acidic pH.

1-[2-(2-Naphthyl)ethyl]-4-(3-trifluoromethyl- phenyl)-1,2,3,6-tetrahydropyridine, referred to hereinbelow by its code number SR 57746, and its pharmaceutically acceptable salts, in particular its hydrochloride, have been described in EP 0,101,381 as anorexigenic agents and, subsequently, as anti-anxiodepressants (U.S. Pat. No. 5,026,716), anticonstipation agents (U.S. Pat. No. 5,109,005), neurotrophic agents (U.S. Pat. No. 5,270,320), anti-free-radical agents (U.S. Pat. No. 5,292,745), cardioprotective agents (U.S. Pat. No. 5,378,709) and as agents which are useful in the treatment of amyotrophic lateral sclerosis (WO 97/15304).

In some of these documents, it is indicated that SR 57746 can be administered in suitable pharmaceutical forms, including the form as a complex with cyclodextrins. However, no complex of this type has ever been described.

The poor solubility of SR 57746 and of its salts in water, in particular hydrochloride (0.03 mg/ml), as well as the instability of the aqueous solutions thus formed, represent a serious problem for the administration and storage of solutions containing this compound. This problem becomes even more serious when it is desired to prepare a drinkable aqueous solution which can be swallowed easily by patients with swallowing problems.

Preliminary studies carried out with standard solubilizing agents, including cyclodextrins (referred to hereinbelow as CDs), have generally led either to insufficient solubilization or to partial degradation of the SR 57746. For example, poor results were obtained with 2-hydroxypropyl-β-CD, α-CD and γ-CD. The methylated derivatives (such as, for example, RAMEB-CD, "randomized methylated β-CD") appeared to give interesting results, but their use in pharmaceutical compositions is, for the time being, not permitted by the European and American pharmacopoeias.

It has now been found that large amounts of SR 57746 hydrochloride can be dissolved, giving stable aqueous solutions, by using β-cyclodextrin, this solubilization being improved at acidic pHs.

More specifically, it has been confirmed that the above components, in given relative amounts, produce aqueous solutions which are stable over time, even under extreme temperature conditions.

Thus, the subject of the present invention is an aqueous solution containing 1-[2-(2-naphthyl)ethyl]-4-(3-trifluoromethylphenyl)-1,2,3,6-tetrahydropyridine hydrochloride (hydrochloride of SR 57746), characterized in that it comprises:
a non-zero amount of β-cyclodextrin (β-CD) of less than or equal to 50 mg/ml;
a non-zero amount of SR 57746 hydrochloride (in mg/ml) of less than or equal to one-tenth of the amount of β-CD expressed in mg/ml;
a pharmaceutically acceptable acid or buffer to give a pH of less than or equal to 3;
with the proviso that, for an amount of β-CD ranging from 30 to 50 mg/ml, the amount of SR 57746 hydrochloride fits the equation:

amount of SR 57746 hydrochloride $$(\text{mg/ml}) \geq \left[ \frac{\text{amount of } \beta - CD \text{ (mg/ml)}}{10} - 3 \right]$$

The SR 57746 hydrochloride can be prepared according to the methods described in EP 101,381 or WO 98/28273.

The β-CD to be used according to the invention is a β-CD in accordance with the tests of the European and American pharmacopoeias.

The pharmaceutically acceptable acids which can be used according to the present invention are, for example, acetic acid, citric acid, tartaric acid, ascorbic acid, lactic acid, succinic acid or fumaric acid.

These acids can be used as they are or included in buffer systems.

Examples of buffers which can be used according to the invention are acetic acid/sodium or potassium acetate systems; tartaric acid/sodium or potassium tartrate systems; lactic acid/sodium or potassium lactate systems; and ascorbic acid/sodium or potassium ascorbate systems.

Citric acid, in anhydrous or hydrated form, in particular citric acid monohydrate, is particularly advantageous for the preparation of the solution of the invention.

According to a preferred aspect, the present invention relates to an aqueous solution based on 1-[2-(2-naphthyl)ethyl]-4-(3-trifluoromethylphenyl)-1,2,3,6-tetrahydropyridine hydrochloride (hydrochloride of SR 57746), characterized in that it comprises
a non-zero amount of β-CD of less than or equal to 50 mg/ml
a non-zero amount of SR 57746 hydrochloride (in mg/ml) of less than or equal to one-tenth of the amount of β-CD expressed in mg/ml
an amount of citric acid ranging from 0.1 mg/ml to 200 mg/ml
with the proviso that, for an amount of β-CD ranging from 30 to 50 mg/ml, the amount of SR 57746 hydrochloride fits the equation:
amount of SR 57746 hydrochloride $$(\text{mg/ml}) \geq \left[ \frac{\text{amount of } \beta - CD \text{ (mg/ml)}}{10} - 3 \right]$$

Preferred solutions according to the present invention comprise an amount of SR 57746 hydrochloride ranging from 0.1 to 2 mg/ml.

According to a preferred aspect, the solutions of the invention comprise an amount of β-CD of between 5 and 15 mg/ml.

According to a particularly preferred aspect, the solutions of the invention comprise an amount of SR 57746 hydrochloride ranging from 0.1 to 1.1 mg/ml, an amount of β-CD of between 5 and 15 mg/ml and an amount of citric acid ranging from 1 to 100 mg/ml, preferably from 5 to 50 mg/ml, advantageously about 10 mg/ml.

Among these solutions, those comprising 0.55 mg/ml or 1.1 mg/ml of SR 57746 hydrochloride, about 10 mg/ml of β-CD and about 10 mg/ml of citric acid are more advantageous.

It has been found, by 2-dimensional coupled NMR tests, that SR 57746 in water forms with the β-CD a complex comprising 2 molecules of β-CD per molecule of SR 57746.

The stoichiometry of this complex was confirmed by microcalorimetry titration studies in aqueous solution in the presence of citric acid monohydrate at about 10 mg/ml.

It has also been found that two molecules of β-CD encapsulate the molecule of SR 57746 in aqueous solution at the two opposite ends of the SR 57746 compound and that the complex thus obtained is not only very soluble but also very stable in aqueous solution.

The complex formed between a molecule of SR 57746 and two molecules of β-CD is novel and constitutes a further subject of the present invention.

The solution can be prepared according to the usual techniques, by mixing in water, in any order, the SR 57746 hydrochloride, the β-CD and the acid or buffer system chosen, in the amounts envisaged by the invention, and stirring the mixture until the constituents have completely dissolved.

The solution can then be purified, for example by ultrafiltration, optionally passed through an autoclave, according to the usual techniques, and then stored as it is or divided into monodose or multidose containers.

The solution according to the present invention can be used in the form of dosage units containing an effective amount of active principle.

Thus, according to another of its aspects, the present invention relates to a drinkable pharmaceutical composition, in dosage units, characterized in that it comprises an aqueous solution as defined above, in which the SR 57746 hydrochloride is present in an amount of from 0.5 to 10 mg per dosage unit, preferably from 1 to 5 mg per dosage unit.

The solution and the composition of the invention can optionally comprise sweeteners or flavouring agents to enhance its taste.

Particularly advantageous pharmaceutical compositions are indicated in Table 1.

TABLE 1

Pharmaceutical compositions in dosage units

| SR 57746 hydrochloride | 2.2 mg | 4.4 mg |
|---|---|---|
| β-CD | 40 mg | 40 mg |
| Citric acid monohydrate | 42 mg | 42 mg |
| Water qs | 4 ml | 4 ml |

Whether or not they have been passed through an autoclave, the pharmaceutical compositions according to the present invention proved to be very stable on storage, under the following conditions:

a temperature of between 5° C. and 40° C.

storage for 3 months.

The compositions of the invention, in dosage units, can be packaged according to the usual practice, for example in glass, polycarbonate, polyvinyl chloride, polyethylene or polypropylene bottles and sealed with pharmaceutically acceptable stoppers, for example stoppers made of chlorobutyl or bromobutyl elastomer, optionally lined with Teflon and covered, where appropriate, with a suitable cap.

EXAMPLE

Solution of SR 57746 at 0.5 mg/ml 220 mg of SR 57746 hydrochloride (corresponding to 200 mg of SR 57746 free base), 4 g of β-CD (Roquette Fréres, in accordance with the tests of the European and American pharmacopoeias) and 4.2 g of citric acid monohydrate in 400 ml of water are mixed together at room temperature, in the open air or in the absence of oxygen or under a cover of nitrogen, in any order, and are stirred until completely dissolved.

4 ml of solution are divided into 9 ml white glass bottles; the bottles are sealed with stoppers made of chlorobutyl elastomer and the stopper is covered with an aluminium cap.

What is claimed is:

1. Aqueous solution containing 1-[2-(2-naphthyl)ethyl]-4-(3-trifluoromethylphenyl)-1,2,3,6-tetrahydropyridine hydrochloride (hydrochloride of SR 57746), characterized in that it comprises:

a non-zero amount of β-CD of less than or equal to 50 mg/ml:

a non-zero amount of SR 57746 hydrochloride (in mg/ml) of less than or equal to one-tenth of the amount of β-CD expressed in mg/ml;

a pharmaceutically acceptable acid or buffer to give a pH of less than or equal to 3;

with the proviso that, for an amount of β-CD ranging from 30 to 50 mg/ml, the amount of SR 57746 hydrochloride fits the equation:

amount of SR 57746 hydrochloride $$(\text{mg/ml}) \geq \left[ \frac{\text{amount of } \beta - CD \text{ (mg/ml)}}{10} - 3 \right].$$

2. An aqueous solution which comprises:

a non-zero amount of β-cyclodextrin of less than or equal to 50 mg/ml:

a non-zero amount of 1-[2-(2-naphthyl)ethyl]-4-(3-trifluoromethylphenyl)-1,2,3,6-tetrahydropyridine hydrochloride (in mg/ml) of less than or equal to one-tenth of the amount of β-cyclodextrin expressed in mg/ml;

a pharmaceutically acceptable acid or buffer to give a pH of less than or equal to 3;

with the proviso that, for an amount of β-cyclodextrin ranging from 30 to 50 mg/ml, the amount of 1-[2-(2-naphthyl)ethyl]-4-(3-trifluoromethylphenyl)-1,2,3,6-tetrahydropyridine hydrochloride is greater than or equal to $$\left[ \frac{\text{amount of } \beta\text{-cyclodextrin (mg/ml)}}{10} - 3 \right]$$

3. A solution according to claim 2, in which the pharmaceutically acceptable acid is chosen from acetic acid, tartaric acid, ascorbic acid, lactic acid, succinic acid, fumaric acid and citric acid, as they are or included in buffer systems.

4. A solution according to claim 3, in which the pharmaceutically acceptable acid is citric acid.

5. A solution according to claim 4, in which the citric acid is present in amounts ranging from 0.1 mg/ml to 200 mg/ml.

6. A solution according to claim 2, which comprises an amount of 1-[2-(2-naphthyl)ethyl]-4-(3-trifluoromethylphenyl)-1,2,3,6-tetrahydropyridine hydrochloride ranging from 0.1 to 2 mg/ml.

7. A solution according to claim 2, which comprises an amount of β- cyclodextrin of between 5 and 15 mg/ml.

8. A solution according to claim 2, which comprises an amount of 1-[2-(2-naphthyl)ethyl]-4-(3-trifluoromethylphenyl)-1,2,3,6-tetrahydropyridine hydrochloride ranging from 0.1 to 1.1 mg/ml, an amount of β-cyclodextrin of between 5 and 15 mg/ml, and an amount of citric acid ranging from 1 to 100 mg/ml.

9. A solution according to claim 8, which comprises 0.55 mg/ml of 1-[2-(2-naphthyl)ethyl]-4-(3-trifluoromethylphenyl)-1,2,3,6-tetrahydropyridine hydrochloride, an amount of β-cyclodextrin of about 10 mg/ml and an amount of citric acid of about 10 mg/ml.

10. A solution according to claim 8, which comprises 1.1 mg/ml of 1-[2-(2-naphthyl)ethyl]-4-(3-trifluoromethylphenyl)-1,2,3,6-tetrahydropyridine hydrochloride, and amount of β-cyclodextrin of about 10 mg/ml and an amount of citric acid of about 10 mg/ml.

11. A drinkable pharmaceutical composition in dosage units, which comprises the aqueous solution according to claim 2, in which the 1-[2-(2 -naphthyl)ethyl]-4-(3-trifluoromethylphenyl)-1,2,3,6-tetrahydropyridine hydrochloride is present in an amount of from 0.5 to 10 mg per dosage unit.

12. A composition according to claim 11, in which the 1-[2-(2-naphthyl)ethyl]-4-(3-trifluoromethylphenyl)-1,2,3,6-tetrahydropyridine hydrochloride is present in an amount of from 1 to 5 mg per dosage unit.

13. A drinkable pharmaceutical composition in dosage units which comprises the aqueous solution according to claim 3, wherein the 1-[2-(2-naphthyl)ethyl]-4-(3-trifluoromethylphenyl)-1,2,3,6-tetrahydropyridine hydrochloride is present in an amount of 1 to 5 mg per dosage unit.

14. A drinkable pharmaceutical composition in dosage units which comprises the aqueous solution according to claim 4, wherein the 1-[2-(2-naphthyl)ethyl]-4-(3-trifluoromethylphenyl)-1,2,3,6-tetrahydropyridine hydrochloride is present in an amount of 1 to 5 mg per dosage unit.

15. A drinkable pharmaceutical composition in dosage units which comprises the aqueous solution according to claim 5, wherein the 1-[2-(2-naphthyl)ethyl]-4-(3-trifluoromethylphenyl)-1,2,3,6-tetrahydropyridine hydrochloride is present in an amount of 1 to 5 mg per dosage unit.

16. A drinkable pharmaceutical composition in dosage units which comprises the aqueous solution according to claim 6, wherein the 1-[2-(2-naphthyl)ethyl]-4-(3-trifluoromethylphenyl)-1,2,3,6-tetrahydropyridine hydrochloride is present in an amount of 1 to 5 mg per dosage unit.

17. A drinkable pharmaceutical composition in dosage units which comprises the aqueous solution according to claim 7, wherein the 1-[2-(2-naphthyl)ethyl]-4-(3-trifluoromethylphenyl)-1,2,3,6-tetrahydropyridine hydrochloride is present in an amount of 1 to 5 mg per dosage unit.

18. A drinkable pharmaceutical composition in dosage units which comprises the aqueous solution according to claim 8, wherein the I-[2-(2-naphthyl)ethyl]-4-(3-trifluoromethylphenyl)-1,2,3,6-tetrahydropyridine hydrochloride is present in an amount of 1 to 5 mg per dosage unit.

19. A drinkable pharmaceutical composition according to claim 12, which comprises 1.1 mg of 1-[2-(2-naphthyl)ethyl]-4-(3-trifluoromethylphenyl)-1,2,3,6-tetrahydropyridine hydrochloride, 40 mg of β-cyclodextrin, 42 mg of citric acid monohydrate and water, the total volume of the composition being 4 ml.

20. A drinkable pharmaceutical composition according to claim 12, which comprises 4.4 mg of 1-[2-(2-naphthyl)ethyl]-4-(3-trifluoromethylphenyl)-1,2,3,6-tetrahydropyridine hydrochloride, 40 mg of β-cyclodextrin, 42 mg of citric acid monohydrate and water, the total volume of the composition being 4 ml.

21. A complex formed between a molecule 1-[2-(2-naphthyl)ethyl]-4-(3-trifluoromethylphenyl)-1,2,3,6-tetrahydropyridine and two molecules of β-cyclodextrin.

* * * * *